US012697460B2

(12) United States Patent　　(10) Patent No.:　US 12,697,460 B2
Rustick　　(45) Date of Patent:　Aug. 4, 2026

(54) METHOD FOR TREATMENT OF DEPRESSION USING SYNAPTIC PATHWAY TRAINING

(71) Applicant: Joseph Rustick, Phoenix, AZ (US)

(72) Inventor: Joseph Rustick, Phoenix, AZ (US)

( * ) Notice: Subject to any disclaimer, the term of this patent is extended or adjusted under 35 U.S.C. 154(b) by 0 days.

(21) Appl. No.: 18/346,605

(22) Filed: Jul. 3, 2023

(65) Prior Publication Data

US 2023/0347101 A1　　Nov. 2, 2023

Related U.S. Application Data

(63) Continuation of application No. 16/827,546, filed on Mar. 23, 2020, now abandoned, which is a
(Continued)

(51) Int. Cl.
　*A61M 21/00*　　(2006.01)
　*A61B 5/16*　　(2006.01)
　*A61N 1/36*　　(2006.01)
(52) U.S. Cl.
　CPC ..... *A61M 21/00* (2013.01); *A61M 2021/0027* (2013.01); *A61M 2021/0044* (2013.01);
(Continued)
(58) Field of Classification Search
　CPC ............ A61N 1/36082; A61N 1/36034; A61N 1/0456; A61N 1/36025; A61N 1/36178; A61N 1/36185; A61N 1/36096
　See application file for complete search history.

(56) References Cited

U.S. PATENT DOCUMENTS 1,012,373 A　　12/1911　Iacoviello
1,023,886 A　　4/1912　Cook
(Continued)

FOREIGN PATENT DOCUMENTS

WO　　2016061320 A2　　4/2016
WO　　2017180589　　10/2017
WO　　2019213551　　11/2019

OTHER PUBLICATIONS

Davis et al. Combining Pharmacotherapy with Cognitive Behavioral Therapy: Traditional and New Approaches Journal of Traumatic Stress, vol. 19, No. Oct. 5, 2006, pp. 571-581 (Year: 2006).*
(Continued)

*Primary Examiner* — Brian T Gedeon
(74) *Attorney, Agent, or Firm* — Schmeiser Olsen, PLLC

(57) ABSTRACT

Disclosed are methods of treating depression, mania, post-traumatic stress disorder (PTSD), and various other neurologic conditions using synaptic pathway training. Methods of synaptic pathway training include, generally, achieving a favorable treatment result by activating a synaptic pathway using a pharmacologic agent, such as treating refractory symptoms of depression with ketamine, following by potentiation of the favorable result by repeatedly stimulating the activated pathway. Stimulation of a synaptic pathway may be achieved by intrinsic means, such as performance of cognitive exercised, or extrinsic means, such as by delivery of a sensory stimulus to the patient, placing a potential voltage difference across the brain or a brain region, or by placing the brain or a brain region in a magnetic field.

9 Claims, 4 Drawing Sheets

Related U.S. Application Data continuation-in-part of application No. 15/787,526, filed on Oct. 18, 2017, now Pat. No. 10,596,378.

(60) Provisional application No. 62/409,753, filed on Oct. 18, 2016.

(52) U.S. Cl.
CPC .............. *A61M 2021/0055* (2013.01); *A61M 2021/0072* (2013.01); *A61M 2021/0077* (2013.01)

(56) References Cited

U.S. PATENT DOCUMENTS

| | | | |
|---|---|---|---|
| 8,676,330 | B2 | 3/2014 | Simon |
| 9,064,036 | B2 | 6/2015 | Hyde et al. |
| 9,649,501 | B2 | 5/2017 | Best |
| 2006/0095088 | A1 | 5/2006 | De Ridder |
| 2008/0208287 | A1 | 8/2008 | Palermo et al. |
| 2011/0224571 | A1 | 9/2011 | Pascual-Leone |
| 2011/0307029 | A1 | 12/2011 | Hargrove |
| 2014/0058189 | A1 | 2/2014 | Stubbeman |
| 2014/0148636 | A1 | 5/2014 | Best |
| 2016/0005320 | A1 | 1/2016 | deCharms |
| 2016/0267809 | A1 | 9/2016 | Decharms et al. |
| 2018/0104490 | A1 | 4/2018 | Rustick |
| 2020/0222656 | A1 | 7/2020 | Rustick |

OTHER PUBLICATIONS

DEA. Gov Ketamine Fact Sheet (Year: 2024).*

Graef et al. Effect of acute NR2B antagonist treatment on long-term potentiation in the rat hippocampus Brain Research vol. 1609, Jun. 3, 2015, pp. 31-39 teaches that ketamine enhances hippocampal activity (Year: 2015).*

Chadi et al. Hippocampal volume and the rapid antidepressant effect of Ketamine J Psychopharmacol May 2015, 29(5): pp. 591-595 (Year: 2015).*

Rodriquez et al. ( Can Exposure-Based CBT Extend IV Ketamine's Effects in Obsessive-Compulsive Disorder? An Open-Label Trial J Clin Psychiatry. Mar. 2016;77(3):408-409 (Year: 2016).*

Cusin et al. (Ketamine augmentation for outpatients with treatment-resistant depression: Preliminary evidence for two-step intravenous dose escalation, Australian & New Zealand Journal of Psychiatry, vol. 51, Issue 1, Jan. 2017, pp. 55-64 (Year: 2017).*

Gilbody et al. Computerised cognitive behaviour therapy (cCBT) as treatment for depression in primary care (REEACT trial): large scale pragmatic randomised controlled trial BMJ Nov. 11, 2015;351:h5627 (Year: 2015).*

Niciu et al. (Ketamine's Antidepressant Efficacy is Extended for at Least Four Weeks in Subjects with a Family History of an Alcohol Use Disorder, International Journal of Neuropsychopharmacology, vol. 18, Issue 1, Jan. 2015, pyu039, https://doi.org/10.1093/ijnp/pyu039 (Year: 2015).*

Wilkinson et al. Cognitive behavior therapy may sustain antidepressant effects of intravenous ketamine in treatment-resistant depression Psychother Psychosom. 2017 ; 86(3): 162-167. doi: 10.1159/000457960 (Year: 2017).*

Andrade Ketamine for Depression, 4: In what Dose, at what Rate, by what Route, for how long, and what frequency? J Clin Psychiatry 78:7, Jul./Aug. 2017 p. 852-857 (Year: 2017).*

Clinical Trials.gov Cognitive Behavioral Therapy prolonging the Antidepressant Effects of IV Ketamine Yale University Starting Feb. 2015 (Year: 2015).*

Garcia-Romeu Psilocybin-occasioned Mystical Experiences in the Treatment ofTobacco Addiction Curr Drug Abuse Rev. 2015;7(3): 157-164 (Year: 2015).*

Ronald S. Duman and George K. Aghajanian, Synaptic Dysfunction in Depression: Potential Therapeutic Targets, HHS Public Access, May 8, 2015, pp. 1-11, Science, New Haven CT.

Adriana Feder, Md, et al., Efficacy of Intravenous Ketamine for Treatment of Chronic Posttraumatic Stress Disorder, JAMA Psychiatry, Jun. 2014, pp. 681-688, vol. 71, No. 6, American Medical Association.

Keith G. Rasmussen, et al., Serial Infusions of Low-Dose Ketamine for Major Depression, Journal of Psychopharmacology 27:5, pp. 444-450, SAGE (2013).

Carlos A. Zarate Jr., MD, et al., Replication of Ketamine's Antidepressant Efficacy in Bipolar Depression: A Randomized Controlled Add-on Trial, NIH Public Access, Jun. 1, 2013, pp. 1-18, Bethesda, Maryland.

Rustick, Joseph, Method for Treatment of Neurological Disorders Using Synaptic Pathway Training, Patent Cooperation Treaty Application Serial No. PCT/US21/22517, Filed Mar. 16, 2021, International Search Report and Written Opinion dated May 27, 2021.

Di Lazzaro et al., "Ketamine Increases Human Motor Cortex Excitability to Transcranial Magnetic Stimulation," J. Physiol 547, 2, pp. 485-496, 2003.

Kandola, et al. "Aerobic Exercise as a tool to improve hippocampal plasticity and function in humans. Practical implications for mental health treatment." Frontiers in Neuroscience, 10, article 373, 2016.

Rodriquez, et al. "Can Exposure-based CBT extend the effects of Intravenous Ketamine in Obsessive-Compulsive Disorder? AN open-label trial" Letters to the Editor, J Clin Psychiatry 77:3, Mar. 2016.

Naqvi, et al. "Preventing cognitive decline in healthy older adults, a review," Canadian Medical Association Journal 185(10), Jul. 9, 2013.

Krystal, John H et al. "Ketamine: A Paradigm Shift for Depression Research and Treatment" Neuron, vol. 101, No. 5, Mar. 6, 2019, pp. 774-778.

Dakwar, Elias et al. "A Single Ketamine Infustion Combined with Motivational Enhancement Therapy for Alcohol Use Disorder: A Randomized Midazolam-Controlled Pilot Trial" American Joural of Psychiatry, vol. 177, No. 2, Feb. 1, 2020, pp. 125-133.

Hasler, "Toward specific ways to combine ketamine and psychology in treating depression," CNS Spectrums, 2020, 25, 445-447, published online Jun. 19, 2019.

Pardham et al. "Ketamine, transcranial magnetic stimulation, and depression specific yoga and mindfulness based cognitive therapy in management of treatment resistant depression: Review and some data on efficacy", Depression Research and Treatment, 2015, Article ID 842817.

Duek et al., "Augmenting the treatment of PTSD with Ketamine - A review", Curr. Treat. Options Psych., 2019, 6, 143-153.

Das et al. "Ketamine can reduce harmful drinking by pharmacologically rewriting drinking memories", Nature Communications, 2019, 10, 5187.

* cited by examiner

METHOD FOR TREATMENT OF DEPRESSION USING SYNAPTIC PATHWAY TRAINING

CROSS REFERENCE TO RELATED APPLICATION

This application is a continuation of U.S. patent application Ser. No. 16/827,546, filed Mar. 23, 2020, which is a continuation-in-part of U.S. patent application Ser. No. 15/787,526, filed on Oct. 18, 2017, now U.S. Pat. No. 10,596,378, which claims priority to U.S. Provisional Patent Application Ser. No. 62/409,753, filed Oct. 18, 2016, the disclosures of which are hereby incorporated entirely herein by reference.

BACKGROUND OF THE INVENTION

Technical Field

This invention relates to methods for the treatment of a neurologic condition. In particular, the invention relates to methods of treating depression, bipolar disorder, mania, alcoholism and post-traumatic stress disorder by training synaptic pathways in the brain and affecting the hippocampus by changing its structure.

State of the Art

Depression is common, and a significant public health problem in the United States. It is estimated that one in ten persons in the U.S. suffer from clinical depression. In addition, studies estimate that one in eight adults (12.7%) in the U.S. meet the diagnostic criteria for alcoholic use disorder.

Persons suffering from depression or bipolar disorder may experience a constellation of debilitating symptoms, including a lack of interest and pleasure in daily activities, significant weight loss or gain, insomnia or excessive sleeping, lack of energy, inability to concentrate, feelings of worthlessness, helplessness, excessive guilt, and recurrent thoughts of death or suicide. Depression can occur as a primary mental health disorder or may arise secondary to an unrelated primary illness. Similarly, alcohol abuse has significant negative physical, social and emotional effects.

Available treatments for depression include cognitive behavioral therapy (CBT), medications, and electroconvulsive therapy (ECT). CBT is effective in many cases, particularly when symptoms are mild to moderate and of recent onset, but less so in chronic or severe depression. CBT has been shown to be more effective with combined with medications, and vise-versa. Treatment of depression with medications is generally safe, however, onset of a therapeutic effect is gradual and may take at least several weeks to manifest, with maximal improvement seen only after eight weeks. If medications are discontinued, the symptoms generally return, often necessitating lifetime pharmacologic therapy. Moreover, medications alone are effective in only forty to sixty percent (40%-60%) of cases, combined CBT and medications are only effective in sixty to seventy percent (60%-70%) of cases. ECT is useful in up to ninety percent (90%) of patients and immediately effective, however, ECT does cause a level of brain damage and is associated with significant side effects, including effects on memory and cognitive impairment. Only about twenty percent (20%) of those with depression receive any treatment, and a significant percentage of those who are treated do not achieve significant or lasting improvement. Available treatments for alcohol abuse include programs such as Alcoholics Anonymous and application often of a twelve-step program and a buddy system to resist the urge to imbibe. Such treatments if they work are quoted as effective in thirteen percent (13%) at five years. It deals with resisting the urge but does not reprogram the individual so they no longer desire alcohol.

Currently available treatments for depression, therefore, are 1) effective only in a subset of patients; and 2) relatively short-lived. Similarly, programs to treat alcoholism have varying degrees of success and are based upon the belief that once an alcoholic always an alcoholic because they don't address the underlying cause.

Accordingly, what is needed is a safe and rapid-onset means for treating depression, bipolar disorder, alcoholism and other related diseases that is widely efficacious and which provides relief of symptoms and urges over an extended period of time.

DISCLOSURE OF EMBODIMENTS OF THE INVENTION

Embodiments of the present invention include methods for treatment of a neurologic condition by synaptic training and treatments effecting the structure of the hippocampus to lessen or eliminate the compulsion to consume alcohol. The foregoing and other features and advantages of the invention will be apparent to those of ordinary skill in the art from the following more particular description of the invention and the accompanying drawings.

Disclosed is a method of treating a neurologic condition by synaptic pathway training comprising steps of activating a synaptic pathway with a pharmacologic agent; and stimulating the activated synaptic pathway. In addition, some of the embodiments of the subject invention combines the application of a preselected drug therapy with a non-drug stimulus therapy to enhance and prolong the drug therapy effect.

In some embodiments, the pharmacologic agent comprises an N-methyl-D-aspartate receptor antagonist. In some embodiments, the pharmacologic agent comprises ketamine. In some embodiments, the pharmacologic agent is a member selected from the group of pharmacologic agents consisting of scopolamine, Namenda, dextromethorphan, amantadine, dextropropoxyphene, and ketobemidone.

In some embodiments, the pharmacologic agent is psilocybin. In some embodiments, the pharmacologic agent is phencyclidine. In some embodiments, the pharmacologic agent is lysergic acid diethylamide. There may be other embodiments, pharmacologic agents which produce additional synaptic connections in specific areas of the brain. These embodiments will treat other conditions reflecting disease processes of specific areas of the brain effected.

In some embodiments, the neurologic condition is depression. In some embodiments, the neurologic condition is bipolar disorder. In some embodiments, the neurologic condition is post-traumatic stress disorder. In some embodiments the condition is alcoholism and possibly other conditions which negatively alter and impact the size and/or functioning of the hippocampus or other areas In some embodiments, stimulating the synaptic pathway comprises performance of a cognitive training exercise. In some embodiments, the stimulating step comprises exposure of a person to a sensory stimulus. In some embodiments, the stimulating step comprises applying a magnetic field to a region of a brain. In some embodiments, the stimulating step comprises applying a potential voltage difference to a region of a brain. In some embodiments, the stimulating step comprises providing an auditory stimulus. In some embodiments, the stimulating step comprises providing a visible-wavelength light stimulus. In some embodiments the initial step is the application of a pharmacological agent followed by a regimen of non-pharmacological cognitive stimuli.

Disclosed is a method of enhancing treatment of a neurologic condition comprising steps treating the condition with a pharmacologic agent to alter the synaptic pathways; and extending a treatment result by repeatedly activating the synaptic pathway with a neural stimulating means.

In some embodiments, activating the synaptic pathway comprises performance of a cognitive training exercise. In some embodiments, activating the synaptic pathway comprises providing an external source of stimulation. In some embodiments, the external source is a magnetic field, a potential voltage difference, an auditory stimulus or a combination of stimuli.

Disclosed is a method of treating a neurologic condition or alcoholism by synaptic pathway training comprising steps activating a synaptic pathway by administering at least one dose of ketamine, at least 0.5 mg/kg; and stimulating the activated synaptic pathway by performing a cognitive exercise for at least thirty (30) minutes daily.

In some embodiments, the neurologic condition is bipolar disorder, depression, mania, or post-traumatic stress disorder.

DETAILED DESCRIPTION OF EMBODIMENTS OF THE INVENTION

Figure 1:
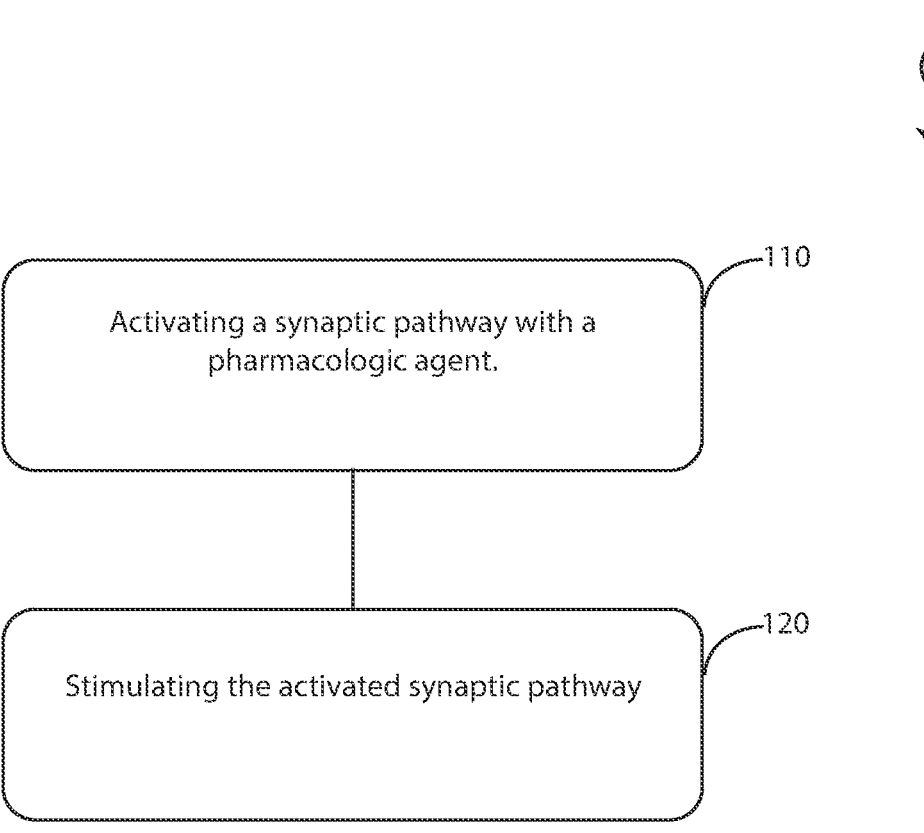
FIG. 1 is a flowchart showing steps of a method for treating alcoholism or a neurologic condition using synaptic pathway training.

As mentioned herein above, the disclosed invention relates to methods for the treatment of alcoholism or a neurologic condition. In particular, the invention relates to methods of treating alcoholism, bipolar disorder, depression, mania, post-traumatic stress disorder, and other neurologic conditions by training synaptic pathways in the brain.

As used herein, the following terms are intended to have a meaning as defined below, unless otherwise indicated.

"Synaptic density" means the number of synapses per unit volume of neural tissue, including brain tissue.

"Synaptic pathway" is used to describe a micro-anatomic pathway communicating a neural impulse between two neurons, wherein the two neurons form a focal anatomic association with one another. The synaptic pathway includes a presynaptic neuron, the anatomic association comprising a synapse, and a postsynaptic neuron.

"Pharmacologic agent" means a biologically active substance delivered to the body with the intent to render a therapeutic effect on a tissue or organ. Pharmacologic agents include any recognized drug and any substance used or acting as a drug.

"Stimulating" means delivering a physiologic provocation with the intent to activate a synapse.

"Cognitive training exercises" means an activity relating to or involving conscious intellectual activity, including but not limited to thinking, reasoning, or remembering.

Chronic or recurrent depression leads to neuroanatomic changes in the brain. Noninvasive brain imaging studies, such as computed tomography and magnetic resonance imaging (MRI), demonstrate volume loss in the hippocampus of patients with chronic or chronically recurring depression. Functional magnetic resonance imaging has been used to show micro-changes in blood flow within multiple regions of the brain in persons suffering from depression. These regions include the hippocampus, areas within the prefrontal cortex, basal ganglia, and limbic system. A corresponding decrease in synaptic density is also seen in these areas of depressed persons.

As discussed herein, currently available treatments for depression include CBT, pharmacologic agents, and ECT. The mechanism of action of antidepressant medications is incompletely understood, however, it is widely believed to involve manipulating levels of neurotransmitters; namely, serotonin, norepinephrine, and dopamine. CBT neuronal mechanisms are not well characterized. To the extent that CBT improves anxiety and depression it must affect the hippocampus, at least in some patients. ECT does not "activate" neurons; rather, ECT causes a simultaneous depolarizing a broad area of brain tissue, and induces seizure activity which spreads neuronal depolarization. This results in brain injury and memory loss and although certain of these therapies may be effective in an individual patient, the beneficial effects of the therapy are typically short-lived, disappearing soon after the therapy is discontinued.

Similarly, alcoholism also negatively effects traffic (synaptic transmissions) through the hippocampus and decreases the size of the hippocampus. Treatment with certain pharmacologicals including but not limited to Ketamine increase both the traffic within and size of the hippocampus. However, these pharmacological treatments are of limited duration such that shortly, generally between nine and twenty-one days, after treatment traffic decreases and the size shrinks to the extent that the symptoms return.

The methods described herein combine pharmacologic and stimulation therapies to achieve a surprising result—temporary improvements in mood and behavior experienced following initial treatment with a pharmacologic agent are made long-lasting by adding stimulation therapy. This combination treatment has been named "synaptic pathway training" because the method "trains" a group of synaptic pathways activated by an initial treatment to continue functioning in the desired way by using regular and repeating neurologic stimulation.

A non-limiting but representative example of such a method is provided. Ketamine is a N-methyl-D-aspartate (NMDA) receptor antagonist with opioid receptor activity. The structure of ketamine comprises an aryl cyclohexylamine. When administered in moderate doses, ketamine acts as a dissociative anesthetic. As an anesthetic, ketamine is rapid acting and has a short duration of action. Because moderate doses do not typically produce decreases in respiration or blood pressure, ketamine is useful in providing anesthesia in children and in various non-hospital settings. Ketamine may be parenterally administered using an intravenous, intramuscular, or trans-nasal route.

Administration of ketamine by intravenous infusion at a dose of about 0.5 milligrams per kilogram of patient body weight (mg/kg) over between about forty-five (45) and about sixty (60) minutes is used to produce relief of symptoms of depression. Higher doses may be used, although doses of about 1.0 mg/kg intravenously over 45 to 60 minutes produces a state of sedation with vivid visual sensory changes. Patients who experience these vivid visual sensory changes, however, experience a stronger anti depressive effect of the treatment. Administration of single-dose intravenous ketamine infusions is also associated with a transient increase in hippocampal volume corresponding with an increase in synaptic density. It is thought that that the increase in hippocampal volume and synaptic density resulting from the administration of single-dose ketamine allows non-depressive thought patterns to occur. This increase in hippocampal volume, synaptic pathways and synaptic density also lessens or eliminates the compulsion for an alcoholic to consume alcohol. Within as little as two hours after an initial treatment of a drug such as ketamine new synapses can be formed in the hippocampus along with the above-mentioned increases in volume and synaptic density.

The anti-depressant effects of ketamine persist from about seven (7) to about twenty-one (21) days, after which symptoms of depression or the urge to consume alcohol begin to re-emerge. If a second dose of ketamine is given by intravenous infusion usually six (6) days after the first dose, symptoms of depression or the urge to consume alcohol do not return until approximately twenty-eight (28) days after the second treatment. Treating depression or alcoholism with two doses of intravenous ketamine six days apart, therefore, may result in as much as approximately thirty-four (34) days of symptom relief.

Stimulation targeting the associated neural synaptic pathways activated by the ketamine, however, results in a profound prolongation of symptom relief. Stimulation may be intrinsic, extrinsic, or a combination of both. "Intrinsic stimulation" is stimulation delivered to the synaptic pathway by the patient engaging in active cognition, whereas "extrinsic stimulation" is the application of an external stimulus, the effects of which passively activate the synaptic pathway without any conscious participation by the patient. With delivery of either an active cognitive or passive sensory stimulus to the activated synaptic pathway, given repeatedly over an extended period of time, relief of symptoms of depression or the urge to consume alcohol can be extended for between twelve months and eighteen months.

For example, one patient with a fifty-year history of bipolar disorder underwent unsuccessful treatment with multiple conventional antidepressant medications and combinations of medications as well as CBT. Following this unsuccessful first-line therapy, multiple treatments with intravenous ketamine resulted in good relief from the depression, but the longest period of relief lasted only approximately twenty-eight (28) days. In an effort to prolong the results of treatment, synaptic training using cognitive activities ("brain HQ exercises") (an intrinsic stimulus) was undertaken for a single session of thirty-minutes each day.

Augmenting the ketamine infusions with synaptic training in this patient resulted in the obliteration of depressive symptoms for greater than one year. Symptoms of mania were also not experienced. The patient characterized the first four-month period starting with the first ketamine dose as feeling the best. The second four-month period, the patient felt "good," but not as well as during the first four-month period. During the third four-month period, the patient still felt much, much better than baseline (prior to ketamine treatment), although was subjectively looking forward to receiving an additional ketamine dose sometime in the future.

In an alcoholic patient he requested treatment for depression and was treated with the standard protocol of a ketamine infusion with a second treatment six days later. This patient was immediately started on synaptic training as well. The patient followed up after more than a year. He reported at that time that he had no symptoms of depression and that he had two and a bottle of beer in the refrigerator. When questioned about the significance of the beer he reported that he no longer drank a bottle of gin a day. At a year and half, he sought another treatment. He lost his job and started drinking vodka. He was given a single IV infusion and no longer had the desire to drink. (He reported that he got another job shortly thereafter.)

A novel aspect of this method is using a pharmacologic agent in combination with a neural stimulation means, whether extrinsic or intrinsic, to subsequently target the brain area (synaptic pathway) activated by the pharmacologic agent. It should be noted that the use of many other pharmacologic agents other than ketamine may be used, depending on the synaptic pathway to be activated and the neurologic condition to be treated. It should also be noted that use of many different means of targeted stimulation of the activated synaptic pathways are also contemplated. It should additionally be noted that alcoholism as well as many neurologic conditions other than depression may be treated with a combination of pharmacologic synaptic pathway activation following by training the activated synaptic pathway with repeated targeted stimulation.

The result of combining pharmacologic activation with targeted stimulation of the activated synaptic pathway is an increase in the efficacy and duration of effect of the treatment much, much longer than with the use of drug therapy or directed synaptic pathway stimulation alone. The exact mechanism of this effect is unknown; however, it is thought that the pharmacologic activation of a synaptic pathway in the brain, resulting in growth of new synapses between the neurons in the pathway, is made durable by "training" the synaptic pathway by regular and repeated stimulation of the pathway's presynaptic neuron.

FIG. 1 is a flowchart showing steps of a method for treating a neurologic condition using synaptic pathway training. In some embodiments, the neurologic condition is depression. "Depression" means either clinical diagnosis of either unipolar or bipolar depression. It should be understood, however, that treatment of many other neurologic conditions using method 100 is contemplated, including mental health conditions such as mania, post-traumatic stress disorder ("PTSD"), schizophrenia, dysthymia, chronic pain syndromes including complex regional pain syndrome, substance abuse disorders including but not limited to alcoholism, neuropathic pain, dysesthesia, traumatic brain injury, and other neurologic illnesses and conditions.

FIG. 1 shows a method 100 comprising an activating step 110 and a stimulating step 120.

Activating step 110, in some embodiments, comprises activating a synaptic pathway with a pharmacologic agent. In some embodiments, the pharmacologic agent comprises an N-methyl-D-aspartate (NMDA) receptor antagonist. For example, as discussed herein, ketamine is an NMDA receptor antagonist used to activate various synaptic pathways associated with relieving symptoms and physical signs depression. Ketamine, other NMDA receptor antagonists, and other pharmacologic agents also activate synaptic pathways of many other neurologic conditions, including but not limited to conditions noted herein above. The pharmacologic agent, in some embodiments, is used to activate synaptic pathways to treat any of these aforementioned of other neurologic conditions.

In some embodiments, the pharmacologic agent is a serotonin receptor agonist, such as psilocybin, for example. In some embodiments, the pharmacologic agent is a muscarinic receptor agonist, such as scopolamine, for example.

Ketamine is administered at a standard dose of about 0.5 milligrams per kilogram body weight ("mg/kg") as an intravenous infusion, in some embodiments. In some embodiments, the dose of intravenous ketamine is about 1.0 mg/kg. In some embodiments, the dose of intravenous ketamine is between about 0.5 mg/kg and about 1.0 mg/kg.

A relief of symptoms of depression indicates activation of the synaptic pathways targeted for training. "Activation" of the synaptic pathway means an increase in the absolute number of functioning synaptic connections between axonal terminals of a presynaptic neuron and dendrites or cell bodies of one or more postsynaptic neurons. In some embodiments, the synaptic pathway is a prefrontal cortex synaptic pathway. In some embodiments, the synaptic pathway is a hippocampal synaptic pathway. In some embodiments, the synaptic pathway is a limbic system synaptic pathway.

The pharmacologic agent, like ketamine, for example, causes an increase in synaptic density between the presynaptic and postsynaptic neurons of the synaptic pathway which correlates to relief from symptoms of depression, or some other neurologic condition including the urge to consume alcohol. As noted herein, some patients experience a relief of depressive symptoms following one dose of intravenous ketamine. Some patients, however, do not experience a full relief of depression until receiving two doses of intravenous ketamine administered usually six (6) days apart. Some patients require greater than two intravenous ketamine doses, each dose following the preceding dose by a period of one to two days. Consequently, in some embodiments, activating step 110 comprises administering two doses of the pharmacologic agent. In some embodiments, activating step 110 comprises administering three doses of the pharmacologic agent. In some embodiments, activating step 110 comprises administering greater than three doses of the pharmacologic agent. There is a direct correlation between providing a therapeutic amount of the pharmacological agent which results in the patient experiencing a temporary dissociative state and achieving a sufficient increase in the number of synapses, hippocampal volume and synaptic density to achieve a reduction or elimination of the targeted symptoms including alcoholism and the urge to consume alcohol. Dosages need to be administered in the lowest amount necessary to achieve the desired temporary dissociative effect without reaching the anesthetic dose. Other hallucinogens such as psychedelics and deliriants may also be effective but typically not at the same time.

Individuals react differently to the pharmacological agents discussed above such as Ketamine for a variety of reasons. It appears while some patients are simply more sensitive others, especially those who have a history of using pharmacologic agents, require a higher dosage to achieve the desired temporary dissociative effect. Accordingly, an initial dosage of 0.5 mg per kilogram of weight is a preferred starting point. This dosage has shown to be effective for relatively young, healthy patients without significant pharmacological (drug) experiences. Where that treatment is not completely effective it is common for the patient to experience improved sleeping patterns. Improved sleep patterns indicate that while the treatment is partially effective a higher dosage is required to obtain the desired temporary dissociative effect. Once the chosen dosage is effective in achieving a temporary dissociative state in the patient there will be an accompanying decrease or elimination of symptoms confirming the described positive changes to the hippocampus. This can be confirmed if necessary, by before and after scans. The described cognitive exercises are initiated immediately after the first treatment to maintain the hippocampal changes for a period far beyond the time achieved with only the pharmacological treatment.

The length of time reduced or eliminated symptoms can be sustained will vary from patient to patient. Assuming adherence to the cognitive exercise protocol it is common to obtain an extension of the desired effect for twelve to eighteen months. As some point the symptoms will begin to gradually appear thus giving the patient time to notify their medical provided and obtain another pharmacological treatment followed by continued cognitive exercises.

Ongoing studies, including brain mapping will correlate particular medical conditions such as those discussed above to particular areas of the brain. Specific pharmacological drugs are then selected for treatment based upon their effect on the particular area which needs to be treated, namely increasing volume, synaptic pathways and synaptic density in the portion of the brain being treated. Similarly, the selected cognitive training exercise or external stimulation is chosen based upon the effect it has on the treated areas of the brain to maintain the increased volume, synaptic pathways and synaptic density.

Stimulating step 120, in some embodiments, comprises stimulating the activated synaptic pathway. The importance of achieving activation of the synaptic pathway prior to performance of stimulating step 120 should be noted, because stimulating step 120 acts to potentiate the activated state, but not to cause activation. Stimulating synaptic or brain pathways that have been activated by prior treatment, such as treatment with ketamine or another pharmacologic agent, for example, potentiate the favorable treatment result. Activation of the synaptic pathway, therefore, must be present for stimulating step 120 to have the intended effect of prolonging the relief of symptoms of the neurologic condition by prolonging the time period wherein the synaptic pathway remains activated.

As noted herein, stimulation of the activated synaptic pathway undertaken during stimulating step 120 may be intrinsic (cognitive) stimulation or extrinsic (sensory) stimulation. Intrinsic (cognitive) stimulation is actively initiated by the patient. Extrinsic (sensory) stimulation is passively received through an extrinsic sensory stimulus.

Cognitive stimulation is delivered to the activated synaptic pathway, in some embodiments, by performance of various cognitive exercises commonly known as "brain training" exercises. The exercises include, but are not limited to, daily cognitive exercises performed for a minimum of about thirty (30) minutes to any longer time wherein the patient is able to focus on the activity. Cognitive exercises comprise games and thought-activities designed to increase attention, memory, problem solving, focus, and the like. An example of a cognitive exercise that may be utilized in stimulating step 120 is a proprietary set of exercises known as " "Brain HQ®" which has been shown to address the pathways resulting from Ketamine treatment for neurological disorders including but not limited to Bipolar and alcoholism A non-limiting example of providing extrinsic stimulation includes placement of a potential voltage difference across the brain. For example, low-voltage direct current devices, such as a transcranial direct-current stimulation device, may be used in some embodiments to provide an extrinsic stimulus to the activated synaptic pathway. The electrodes to create the potential are positioned with a polarity to depolarize the pre- and post-synaptic neurons of the synaptic pathway.

Additional examples of providing extrinsic stimulation include placing the brain in a magnetic field. In some embodiments, the extrinsic stimulus comprises a sound. In some embodiments, the extrinsic stimulus comprises light. In some embodiments, the extrinsic stimulus comprises a tactile stimulus, such as a touch or a vibration delivered to an area of the body.

In some embodiments, cognitive stimulation comprises periods of physical aerobic exercise. In some embodiments, the period of exercise is less than about twenty (20) minutes per day. In some embodiments, the period of exercise is between about twenty (20) and about forty-five (45) minutes per day. In some embodiments, the period of exercise is between about forty-five (45) minutes and about one (1) hour per day. In some embodiments, the period of exercise is greater than about one 1) hour per day.

Figure 2:
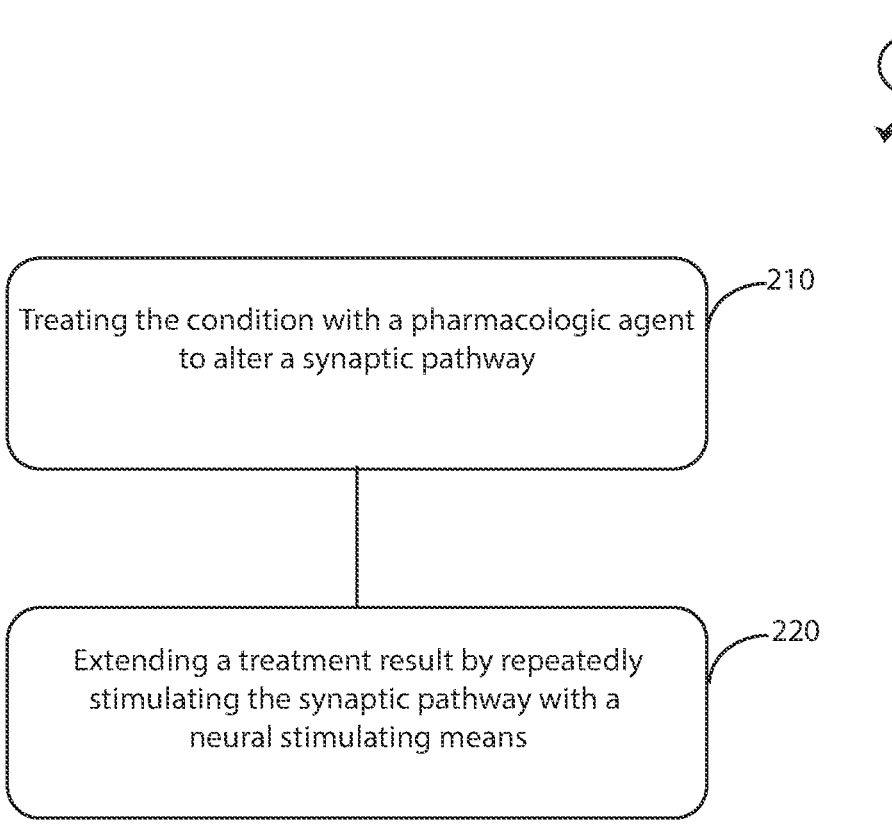
FIG. 2 is a flowchart showing steps of an additional method for treating alcoholism or a neurological condition using synaptic pathway training.

FIG. 2 is a flowchart showing steps of a method for treating a neurologic condition using synaptic pathway training. As shown by FIG. 2, method 200 comprises a treating step 210 and an extending step 220.

Neurologic conditions successfully treated using method 200 include depression, bipolar disorder, alcoholism, mania and PTSD. Use of method 200 is effective, durable, and does not create any of the side-effects associated with long-term therapy with pharmacologic agents, ECT, or other currently available treatments. Moreover, wherein ketamine is used as the synaptic pathway altering agent, relief from sleep disorders—particularly insomnia—which accompany depression, mania, and PTSD is immediate and persists for months, so long as regular stimulation of the activated synaptic pathway undertaken in the extending step continues. The use of method 200 to treat mania or the manic component of bipolar disease is particularly effective. Currently, treatment of mania requires use of psychotropic medications with a very high incidence of undesirable side effects, including weight gain, increased risk of type-2 diabetes, hypercholesterolemia, dysphoria/apathy from blunted moods, and tardive dyskinesia. Method 200 is dramatically effective for the treatment of mania, in some persons, and none of the aforementioned side effects have been observed.

Method 200 is particularly useful in treating persons with PTSD, for at least four reasons. First, method 200 is an effective treatment for PTSD. Second, initial activation of the synaptic pathway may be accomplished immediately, essentially, during the treating step. Third, means for provision of regular stimulation to the activated synaptic pathway, particularly intrinsic cognitive means, are readily available in field-settings, including some battlefield settings. Four when used in the setting of PTSD with TBI (Traumatic Brain Injury) it may help reverse the TBI particularly if done shortly after the TBI occurs. Use of method 200, therefore, is particularly efficacious for use during deployment, where rapid, simple, and durable treatment of PTSD and PTSD/TBI in a soldier is essential.

Treating step 210, in some embodiments, comprises treating the neurologic condition with a pharmacologic agent to alter a synaptic pathway. The neurologic condition may be depression, bipolar disease, dysthymia, or any number of other neurologic conditions including, but not limited to, those neurologic conditions listed herein. "Treating" means administering one or more therapies over one or more discrete time periods with the intent to either treat the condition, cure the condition, or relieve symptoms caused by the condition. The therapies may comprise: administration of a pharmacologic agent; administration of a treatment, such as transcranial direct-current stimulation; or the like. Alteration of the synaptic pathway means "activation" of the pathway manifest directly by an increase in synaptic density, or manifest indirectly by relief of improvement of symptoms of the neurologic condition.

Extending step 220, in some embodiments, comprises extending a treatment result by repeatedly stimulating the synaptic pathway with a neural stimulating means. "Extending a treatment result" means causing the favorable results of treatment resulting from treating step 210 to remain manifest for a period of time longer than that period absent extending step 220. In some embodiments, extending step 220 comprises stimulating an activated synaptic pathway with an intrinsic stimulus, as described herein. In some embodiments, extending step 220 comprises stimulating an activated synaptic pathway with an extrinsic stimulus, as described herein. In some embodiments, extending step 220 comprises performance of physical exercise during recurring periods, such as daily, for a period of days, weeks, or months.

Figure 3:
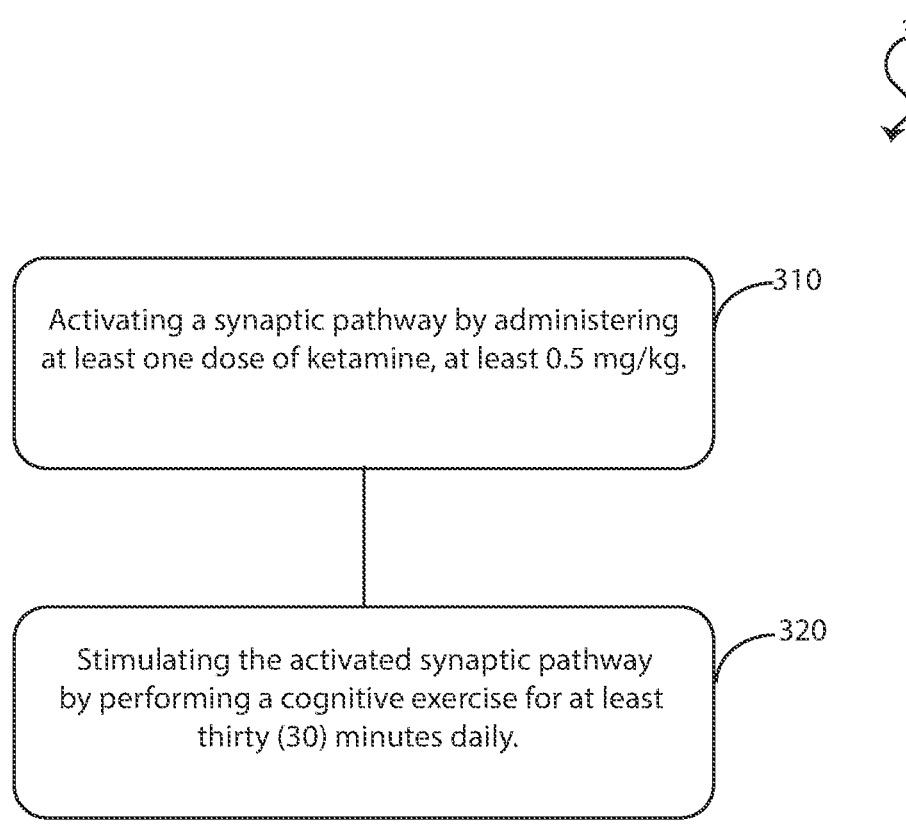
FIG. 3 is a flowchart showing steps of another method for treating alcoholism or a neuroglial condition using synaptic pathway training.

FIG. 3 is a flowchart showing steps of another method for treating a neurological condition using synaptic pathway training. FIG. 3 shows a method 300 for treating a neurological condition comprising an activating step 310 and a stimulating step 320. In some embodiments, the neurologic condition is depression. In some embodiments, the neurological condition is mania or bipolar disease. In some embodiments, the neurological condition is PTSD.

In some embodiments, activating step 310 comprises activating a synaptic pathway by administering at least one dose of ketamine, at least 0.5 mg/kg. This is a baseline dose, which may need to be repeated one or more times, at intervals of about one to two (1-2) days. It is foreseeable that some patients would respond more readily to a higher dose, up to the 1.0 mg/kg dose which is typically used to induce a dissociated state of anesthesia. The dose may need to be repeated two, three, or more times to obtain the desired level of relief. Relief of symptoms is the clinical marker which indicates activation of the synaptic pathway following completion of activating step 310, prior to performing stimulating step 320.

In some embodiments, stimulating step 320 comprises stimulating the activated synaptic pathway by performing a cognitive exercise for at least thirty (30) minutes each day.

Figure 4:
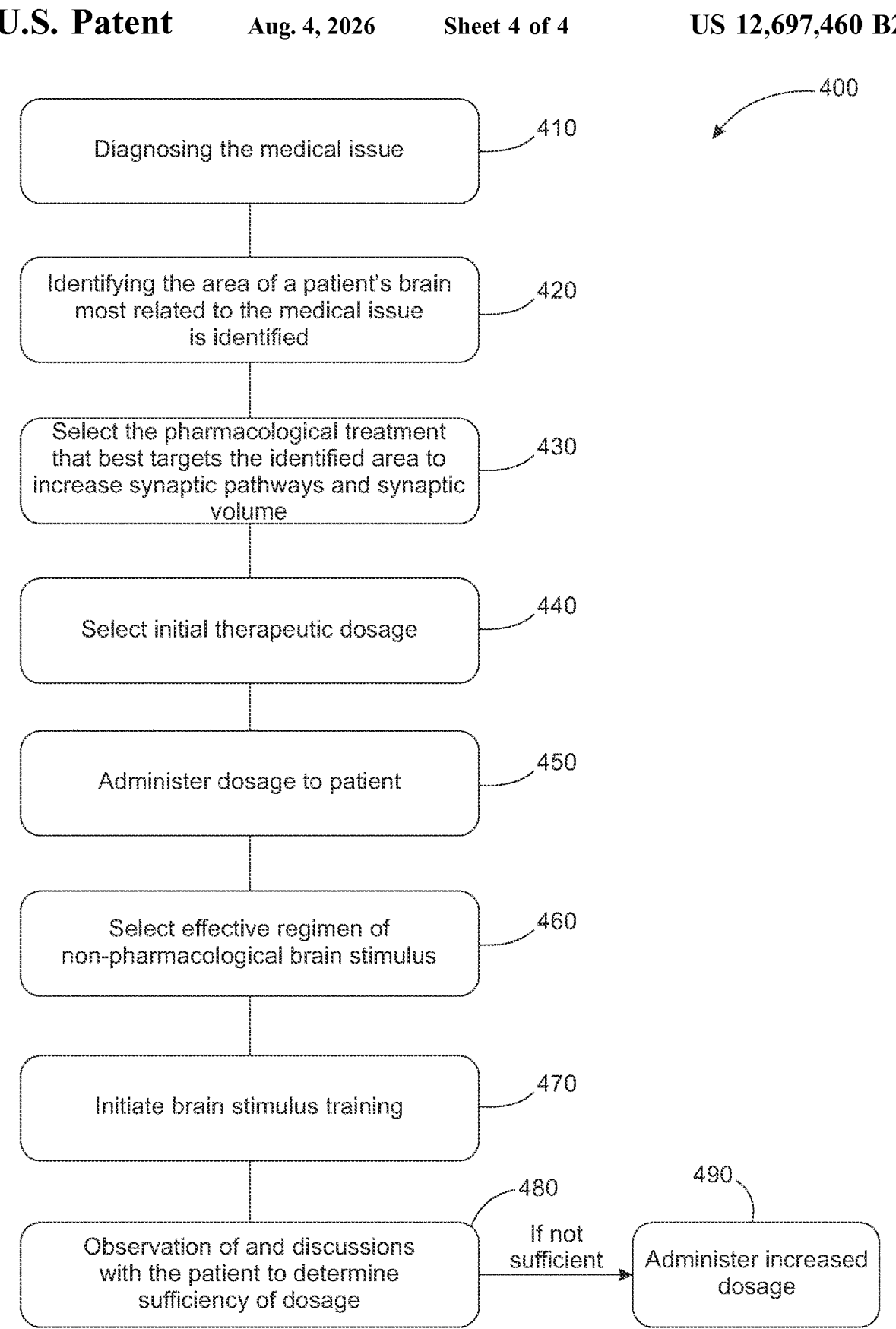
FIG. 4 is a flowchart showing more detailed steps of another method of treatment for alcoholism or other neurological condition.

FIG. 4 is a flowchart showing steps of another method for treating a neurological condition using synaptic pathway training. FIG. 4 shows a method 400 for treating a neurological condition comprising initially consulting with a patient to be treated the medical provider will start by diagnosing the issue step 410. Once diagnosed the area of the brain most related to that issue is identified step 420. The pharmacological treatment, including but not limited to a dissociative or hallucinogenic which creates a positive effect on that portion of the brain by increasing synaptic pathways and synaptic density (synaptic volume) is selected step 430. A therapeutic dosage is selected to achieve and increase in structures such as volume, synaptic pathways and synaptic density step 440 and administered to the patient step 450. Once the sought-after increase in structure are obtained a regimen of nonpharmacological brain stimulus is selected that effects the targeted area of the brain to maintain the increased structural changes step 460, and the brain stimulus training is initiated step 470. Observation of and discussions with the patient determines whether the dosage was sufficient to achieve patient experience step 480 indicating the desired increases in structure step 490.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above.

What is claimed is:

1. A method of treating a patient having a neurologic condition by synaptic pathway training comprising steps:

altering synaptic pathways within an area of the patient's brain with a pharmacologic agent hallucinogenic administered intravenously in a dosage of at least 0.5 mg per kilogram of the patient's weight adjusted to a greater dosage amount as needed based on the patient to obtain a temporary dissociative effect, wherein the hallucinogenic pharmacologic agent is selected based on its effectiveness in increasing hippocampal volume, synaptic pathways, and synaptic density in the hippocampus, wherein altering synaptic pathways comprises increasing hippocampal volume, increasing and activating synaptic pathways, and increasing synaptic density within a hippocampus of the patient's brain;

stimulating the altered synaptic pathways with cognitive stimulation exercises, wherein the cognitive stimulation exercises are selected based on their efficacy in maintaining the increased hippocampal volume, synaptic pathways, and synaptic density and wherein the cognitive stimulation exercises are initiated within 48 hours after administering the pharmacologic agent; and extending a treatment result by repeatedly stimulating the altered synaptic pathway with a daily cognitive exercise, selected from the cognitive stimulation exercises, for a minimum of thirty minutes, wherein the daily cognitive exercise comprises engagement with software based cognitive programs designed to increase attention, memory, problem solving, and focus to maintain the increased hippocampal volume, increased synaptic pathways, and increased synaptic density within a hippocampus.

2. The method of claim 1, wherein prior to the stimulating step there is a selecting step wherein the non-pharmacological treatment is chosen based upon its efficacy in maintaining said synaptic pathways and volume.

3. The method of claim 2, wherein prior to the altering step there is a step of choosing the pharmacological agent based upon the agent's effectiveness in increasing synaptic pathways and synaptic volume in an area of the brain associated with the neurological condition.

4. The method of claim 3, including interviewing the patient to determine whether the dosage was sufficient to increase synaptic pathways and synaptic volume.

5. The method of claim 4, including administering an increased dosage when it is determined the initial dosage was insufficient.

6. The method of claim 4, wherein the neurologic condition is depression.

7. The method of claim 4, wherein the neurologic condition is bipolar disorder.

8. The method of claim 4, wherein the neurologic condition is post-traumatic stress disorder.

9. The method of claim 1, wherein the neurological condition is alcoholism.

* * * * *